(12) United States Patent
Delhom

(10) Patent No.: US 9,392,792 B1
(45) Date of Patent: Jul. 19, 2016

(54) TOPICAL COMBINATION OF FIPRONIL, PERMETHRIN AND PYRIPROXYFEN

(71) Applicant: VIRBAC, Carros (FR)

(72) Inventor: Nathalie Delhom, Vence (FR)

(73) Assignee: VIRBAC, Carros (FR)

( * ) Notice: Subject to any disclaimer, the term of this patent is extended or adjusted under 35 U.S.C. 154(b) by 0 days.

(21) Appl. No.: 14/585,804

(22) Filed: Dec. 30, 2014

(51) Int. Cl.
- A01N 53/00 (2006.01)
- A01N 25/02 (2006.01)
- A01N 43/40 (2006.01)
- A01N 47/02 (2006.01)

(52) U.S. Cl.
CPC ............... *A01N 53/00* (2013.01); *A01N 25/02* (2013.01); *A01N 43/40* (2013.01); *A01N 47/02* (2013.01)

(58) Field of Classification Search
None
See application file for complete search history.

(56) References Cited

U.S. PATENT DOCUMENTS

| 6,867,229 B2 | 3/2005 | Etchegaray | |
|---|---|---|---|
| 2013/0225516 A1* | 8/2013 | Soll | A61K 9/0017 514/28 |

FOREIGN PATENT DOCUMENTS

| WO | 9712521 | 4/1997 |
|---|---|---|
| WO | 02062326 A1 | 8/2002 |
| WO | 2008080542 A2 | 7/2008 |
| WO | 2009033175 A1 | 3/2009 |
| WO | 2011038024 A1 | 3/2011 |

OTHER PUBLICATIONS

"Label Amendment—Acceptance of Master Labeling Submitted for Implementation of Pet Spot-On Mitigation Product Name: EFFITIX® Plus Topical Solution for Dogs," Sep. 11, 2014.

* cited by examiner

*Primary Examiner* — Jennifer Berrios

(74) *Attorney, Agent, or Firm* — Law Office of Salvatore Arrigo and Scott Lee, LLP

(57) ABSTRACT

The present invention relates to a liquid topical veterinary pharmaceutical composition consisting of fipronil, permethrin at high concentration and pyriproxyfen such that it does not crystallize when it is applied to the coat of an animal, and to the use thereof in the prevention and/or treatment of infestations of domestic animals by external parasites. The present invention also relates to the use of pyriproxyfen as an inhibitor of the crystallization of a liquid formulation comprising fipronil and permethrin at high concentration.

8 Claims, No Drawings

TOPICAL COMBINATION OF FIPRONIL, PERMETHRIN AND PYRIPROXYFEN

The present invention relates to a liquid topical veterinary pharmaceutical composition combining fipronil, permethrin and pyriproxyfen for the treatment of infestations by external parasites.

Pets are often infested with one or more parasites which feed on blood, such as dog or cat fleas, ticks, or else mites (responsible for mange).

Fleas are wingless insects, with a body that is laterally compressed and with highly developed legs, adapted for jumping. They are ectoparasites, which suck blood from mammals or birds. The some 2000 species listed belong to the order Siphonaptera. Two species of fleas are commonly encountered in Europe; they are the cat flea (*Ctenocephalides felis*) and the dog flea (*Ctenocephalides canis*) which live in the fur of the animals.

Flea bites cause itching, in animals and in humans. The saliva of the flea (secreted at each bite) can also, depending on the individual, lead to immediate or delayed allergic reactions. These reactions result in various skin lesions and itching.

The fleas of the *Ctenocephalides* genus are, moreover, intermediate hosts of *Dipylidium caninum*, which is a parasitic worm of the small intestine of dogs and cats. Carnivores become infested by swallowing the parasite-infested fleas. This infestation can cause anal pruritus, engorgement of the anal sacs, and also dermatitis of the perineal region. This is why it is sometimes recommended to regularly worm animals in addition to controlling fleas.

Ticks (*Rhipicephalus* sp., *Ixodes* sp., *Dermacentor* sp., *Amblyomma* sp., etc) can also cause the animal stress and be harmful to its health. They can also be harmful to humans. However, the most serious problem with ticks is that they are a vector for pathogenic agents which can affect both animals and humans. Among the major diseases that must be prevented, mention may be made of borreliosis (Lyme disease caused by *Borrelia burgdorferi*), babesiosis (piroplasmosis caused by *Babesia* sp.) and rickettsiosis. Ticks can also release toxins with paralyzing and inflammatory, and sometimes lethal, properties.

Mange (*Demodex* sp., *Sarcoptes* sp., *Otodectes* sp., etc) is particularly difficult to combat since there are very few effective active materials; it requires frequent treatments.

Mosquitoes (*Culex* sp., *Aedes* sp., *Anopheles* sp., etc) have an extremely important role in human or animal health since they concentrate, beyond their role as pests through the bites that they inflict, the largest group of vectors of pathogenic agents transmissible to human beings, including numerous zoonoses. They are vectors of three groups of agents that are pathogenic for human beings: *Plasmodium*, filaria and also numerous arboviruses. They are present on all the landmasses of the planet (with the exception of Antarctica), in forests, savannah or urban environments, as soon as a surface of fresh or brackish water, even small or temporary, is available. Sixty-five species are referenced in metropolitan France.

Sand flies (*Phlebotomus* sp., etc) are haematophagous insects. The sand fly is a vector insect. If it is infected, its bite transmits leishmaniasis.

Infestations by these various parasites, and quite particularly by fleas, therefore represent a significant health problem for the animals which are infested and make it necessary to be able to have suitable treatments available; it thus appears to be advantageous to combine different active agents in order to broaden the spectrum of action of the formulations developed.

In the context of its studies, the applicant has sought to develop a liquid skin formulation, which is easy to administer, combining several ectoparasiticides, in particular fipronil and permethrin at a high concentration (greater than 50% by weight/volume); in this context, it has encountered problems of crystallization of these formulations on the coat of the animals when they are applied by cutaneous deposition (administration termed spot-on).

Formulations of ectoparasiticides, such as those combining derivatives of N-phenylpyrazole and of permethrin, have been known for a long time since the overlapping and the complementarity of the spectra of actions of the active agents makes them particularly advantageous in controlling parasites in agriculture and in the veterinary field where each of the active agents is commonly used.

Through the conducting of comparative tests for crystallization, on glass slides, of various combinations of active agents, the applicant has noted that a liquid composition combining fipronil and permethrin at high concentration (at least 50% by weight/volume) crystallizes on a glass slide, whereas this crystallization is prevented when pyriproxyfen is added to the combination (see experimental section); it has also demonstrated that such a liquid formulation combining fipronil, permethrin at high concentration and pyriproxyfen does not crystallize during its storage.

The appearance of crystals on the coat of animals during the application of a liquid veterinary composition is bothersome and it is sought to avoid it; indeed, it gives the treated animal a dirty and dusty appearance. In addition, once crystallized, the active material of the composition can easily detach from the hairs due to any movements and rubbing by the animal, the obvious consequence of which is to prevent the therapeutic action of the treatment. Moreover, dissemination of the active material can take place in the environment and can contaminate the latter, and this must be avoided as much as possible.

The applicant has thus given itself the objective of developing a product for the prevention and treatment of infestations by external parasites, in particular fleas, in domestic animals, which has a broad spectrum of action, which is easy to administer, while having a rapid and persistent action, and the application of which to the coat of animals prevents as much as possible the appearance of crystals visible to the naked eye.

Fipronil is a molecule of the family of N-phenylpyrazoles, which are compounds that have a very broad spectrum of activity, including anti-parasitic activities; they are described in patent applications EP 0 295 117 and EP 0 352 944.

Permethrin, or (3-phenoxyphenyl)methyl(1RS,3RS,1RS,3SR)-3-(2,2-dichlorovinyl)-2,2-dimethylcyclopropane-1-carboxylate (CAS No. 52645-53-1), has the following chemical structure:

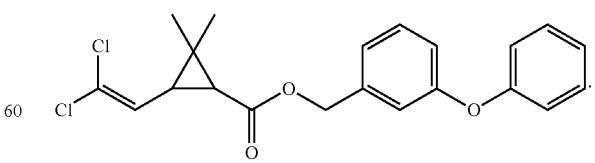

It is a powerful neurotoxic insecticide of the pyrethroid family.

Pyriproxyfen is a larvicidal insecticide, which is a pyridine derivative, having the following chemical structure:

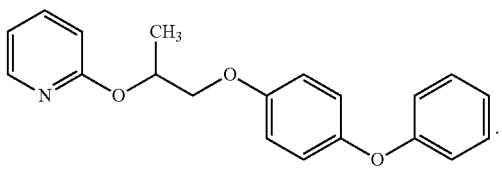 [SMILES: CC(COc1ccc(Oc2ccccc2)cc1)Oc1ccccn1]

It is a juvenile hormone analogue which prevents larvae from developing into an adult insect capable of reproducing.

International application WO 2011/038024 describes a pesticidal composition for spot-on administration, comprising low concentrations of active agents in order to limit as much as possible the adverse side effects; it proposes in particular the combination of fipronil and a pyrethroid; the active agents as a whole are present in a content of less than 20% by weight of the total composition and no problem of crystallization of the active agents during administration of the composition is described.

International application WO 2009/033175 describes an anti-parasitic veterinary composition comprising two insect growth inhibitors (IGRs) and an adulticidal ectoparasiticide such as a synthetic pyrethroid; it is preferably formulated in aerosol form with, as recommended carriers, N,N-dimethyloctanamide and diisopropyl adipate (DIPA). It is mentioned that crystallization of the conditioned product should be avoided so as not to reduce the efficacy of the product; however, it is neither indicated whether this object is achieved, nor how it might be achieved.

International application WO 2008/080542 proposes a formulation combining an N-arylpyrazole and a pyrethroid in a self-spreading formulation, the use of which does not present any risk, and in which no reduction in the effect of the N-arylpyrazole that might be due to the addition of one or more other active agent(s) is observed. The formulation developed in the context of this invention comprises, in addition to the active agents, an aliphatic cyclic carbonate (ethylene carbonate or propylene carbonate) and a cyclic or non-cyclic, aliphatic polyether (in particular, diethylene glycol monoethyl ether); it is preferably topical for spot-on administration. This application makes no mention of an active agent crystallization problem; it should, however, be noted that no example of a composition comprises a permethrin content greater than 45 mg/100 ml.

International application WO 97/12521 describes an antiparasitic composition comprising:
  an N-phenylpyrazole, in particular fipronil;
  an inhibitor of the crystallization of the product during application thereof to the coat of the animal; it is preferably a combination of a surfactant (polysorbate 80) and of a film-forming agent (PVP, polyvinyl alcohol and vinyl acetate/vinylpyrrolidone copolymers);
  an organic solvent; and
  an organic co-solvent.

The crystallization problem addressed in this application aims to prevent solid particles of formulation from being visible on the animal's coat; this problem is solved using the abovementioned crystallization inhibitor.

Patent application EP 1 372 622 emphasizes the advantage of formulating compositions with a high content of pyrethroids, in particular of permethrin, but it also teaches that such compositions have a tendency to crystallize at low temperature and when the pyrethroid is present in a high concentration (for instance contents greater than 50% or than 65% volume/volume). It thus proposes remedying this problem by formulating the pyrethroid(s) in an excipient composed of terpene or of a terpene derivative or of a mixture of an alkyl glycol ether with a terpene or a terpene derivative, in order to prevent or minimize crystallization of the pyrethroid(s) at low temperature.

The research carried out by the applicant has enabled it to note that the problem of crystallization on the coat observed with liquid formulations comprising the combination of fipronil and permethrin at high concentration can be solved by adding pyriproxyfen thereto. The applicant has thus very surprisingly demonstrated that pyriproxyfen acts as an inhibitor of the crystallization of the combination of fipronil and permethrin at high concentration, i.e. greater than or equal to 50% by weight/volume.

Thus, the present invention relates to a liquid topical veterinary pharmaceutical composition consisting of:
  between 2% and 10% of 5-amino-1-[2,6-dichloro-4-(trifluoromethyl)phenyl]-4-(trifluoromethylsulphinyl)-1H-pyrazole-3-carbonitrile (fipronil);
  at least 50% of permethrin;
  between 1% and 10% of pyriproxyfen;
  optionally, one or more antioxidants;
  in solution in an organic solvent chosen from propylene glycol monomethyl ether, dipropylene glycol n-butyl ether, ethylene glycol monomethyl ether, ethylene glycol monoethyl ether, diethylene glycol monoethyl ether and propylene glycol, and mixtures thereof (in the subsequent text and unless otherwise indicated, the percentage ranges are expressed by weight relative to the total volume of the composition).

The use of the term "consisting of" signifies that, according to one particular embodiment of the invention, the composition does not comprise ingredients other than those explicitly mentioned.

According to particular embodiments of the invention, the composition comprises an amount of permethrin of between 50% and 70% by weight/volume, between 50% and 60% by weight/volume, between 50% and 58% by weight/volume and between 50% and 55% by weight/volume.

According to another particular embodiment of the invention, the composition comprises between 6% and 7% by weight/volume of fipronil, and between 50% and 70% by weight/volume, between 50% and 60% by weight/volume, between 50% and 58% by weight/volume and between 50% and 55% by weight/volume of permethrin.

Preferably, the pyriproxyfen concentration in the composition according to the invention is between 1% and 5% by weight/volume, preferentially between 2% and 3% by weight/volume and more preferentially it is 2% by weight/volume.

Among said organic solvents, diethylene glycol monoethyl ether is quite particularly preferred.

The antioxidants are advantageously chosen from ethyl or propyl gallate, α-tocopherol, ascorbic acid, ascorbyl palmitate, monothioglycerol, butylated hydroxytoluene (BHT) and butylated hydroxyanisole (BHA); preferably, BHT or a mixture of BHT and BHA will be used as antioxidant.

When it (they) is (are) present, the antioxidant(s) preferably represent(s) approximately from 0.005% to 2% by weight/volume, and even more preferentially from 0.01% to 0.1% by weight/volume.

According to one preferred variant, the composition according to the invention consists of:
  between 5% and 10% by weight/volume of fipronil;
  between 50% and 70% by weight/volume of permethrin;
  between 1% and 10% by weight/volume of pyriproxyfen;

optionally, between 0.005% and 2% by weight/volume of BHT and/or BHA;

in solution in an organic solvent as defined above.

According to a preferred variant, the composition according to the invention consists of:
- between 5% and 10% by weight/volume of fipronil;
- between 50% and 60% by weight/volume of permethrin;
- between 1% and 5% by weight/volume of pyriproxyfen;
- between 0.005% and 2% by weight/volume of BHT and/or BHA;

in solution in an organic solvent as defined above.

According to a particular variant, the composition according to the invention consists of:

| | |
|---|---|
| Fipronil | 6.7% |
| Permethrin | 50% |
| Pyriproxyfen | 2% |
| BHA | 0.02% |
| BHT | 0.01% |
| Diethylene glycol monoethyl ether | qs 100 ml | composition expressed as percentage by weight relative to the total volume of the composition.

According to a preferred variant, the composition according to the invention consists of:

| | |
|---|---|
| Fipronil | 6.7% |
| Permethrin | 50% |
| Pyriproxyfen | 2% |
| BHA | 0.03% |
| BHT | 0.02% |
| Diethylene glycol monoethyl ether | qs 100 ml | composition expressed as percentage by weight relative to the total volume of the composition.

The compositions according to the invention which are active against blood-sucking parasites, and in particular against fleas, can be in particular in the form of cutaneous liquid compositions or solutions which are very easily applied, just once, at one or more spots, topically, directly to the animal's skin, generally between the shoulder blades (spot-on application). The liquid compositions are therefore packaged in containers which enable the metering of said compositions, and the volume of which is less than or equal to 10 ml, and preferably between 0.1 and 10 ml and more preferentially between 0.3 and 10 ml.

According to one particular embodiment of the invention, it relates to a liquid topical veterinary pharmaceutical composition consisting of:
- between 2% and 10% of 5-amino-1-[2,6-dichloro-4-(trifluoromethyl)phenyl]-4-(trifluoromethylsulphinyl)-1H-pyrazole-3-carbonitrile (fipronil);
- at least 50% of permethrin;
- between 1% and 10% of pyriproxyfen;
- optionally, one or more antioxidants;
- at least one additional active agent such as a pesticide and/or biocides within the meaning of the European directives; said additional active agent broadens or completes the spectra of action of the active agents already present in the compositions according to the invention;
- in solution in an organic solvent chosen from propylene glycol monomethyl ether, dipropylene glycol n-butyl ether, ethylene glycol monomethyl ether, ethylene glycol monoethyl ether, diethylene glycol monoethyl ether and propylene glycol, and mixtures thereof (in the subsequent text and unless otherwise indicated, the percentage ranges are expressed by weight relative to the total volume of the composition).

Said additional active agent(s) is (are) such that the content thereof does not exceed 10% by weight relative to the total volume of the composition and preferentially does not exceed 5% and even more preferentially 3% by weight relative to the total volume of the composition.

The pharmaceutical composition according to the invention is preferably packaged in single-dose pipettes.

The pipettes can consist of one or more films, the constituent material of which can be chosen from polypropylene (PP), polyvinyl chloride (PVC), polyvinylidene chloride, cyclic olefin copolymer (COC), polychlorotrifluoroethylene (PCTFE), or derivatives thereof, taken alone or as a mixture. Preferably, the film is the Polybar™ sold by the company Alcan Packaging™, which consists of a film of cyclic olefin copolymer (COC) co-extruded between two layers of polypropylene (PP). The Polybar is then backed or laminated with a Barex™ film. Other films of different nature can be used alone or in combination with the previous films in order to form the pipette. The material thereof can be chosen from polyethylene terephthalate (PET), polyamide, aluminium or the polyacrylonitrile sold by the company BP Chemicals™ under the brand name Barex™, or derivatives thereof, taken alone or in combination.

The volume of the composition according to the invention contained in the pipettes may be 0.44 ml, 1.1 ml, 2.2 ml, 4.4 ml or 6.6 ml. Generally, the volume is between 0.1 and 10 ml, preferentially between 0.3 and 6.6 ml and even more preferentially between 0.44 and 6.6 ml.

Another subject of the present application relates to a liquid pharmaceutical composition as previously described, as an anti-parasitic veterinary medicament for topical application, preferably spot-on application, for use thereof in the prevention (protection against) and/or treatment of infestations by external parasites, such as fleas, ticks, mosquitoes, sand flies and mites, in domestic animals, in particular in dogs.

The present invention also relates to a method for the prevention and/or the treatment of infestation by external parasites, such as fleas, ticks, mosquitoes, sand flies and mites, in domestic animals, in particular in dogs, comprising the administration, preferably the topical administration, more preferably the administration by spot-on application, of a therapeutic effective amount of the liquid pharmaceutical composition as previously described.

According to this use, the preferred administration (spot-on application) is such that said medicament is intended to be applied by direct deposit on the skin of the animal, at the level of the shoulder blades or along a dorsal line starting from the base of the tail and going back up to the neck.

The amount of medicament to be administered can range from approximately 0.3 to 6.6 ml in dogs, depending on the weight of the animal under consideration, and on the dosage to be adjusted according to the frequency of the treatment.

The present invention also relates to the use of pyriproxyfen as an inhibitor of the crystallization of a topical veterinary composition comprising fipronil and permethrin at a concentration greater than or equal to 50% by weight/volume; preferably, this use is such that the pyriproxyfen is between 1% and 10% by weight/volume and that the fipronil is between 5% and 10% by weight/volume.

The term "inhibitor of the crystallization" is intended to mean a compound which, when it is added to a formulation, reduces or eliminates the appearance of crystals during the application of said formulation to the coat of an animal.

Finally, the present invention relates to a method for preventing the crystallization of a concentrated liquid topical veterinary pharmaceutical composition consisting of fipronil and permethrin at high concentration greater than or equal to 50% by weight/volume, which consists in adding to the composition between 1% and 10% by weight/volume of pyriproxyfen.

EXAMPLES

The objective of the developments carried out is the development of a formulation such that the active agents do not crystallize when they are applied to the coat of animals, despite a high concentration of active agents, in particular of permethrin.

Tests aimed at observing the formation of crystals with the naked eye after deposition of various compositions on glass plates were carried out.

| Compositions tested | | | | | | |
|---|---|---|---|---|---|---|
| Composition | R1 | C1 | C2 | C3 | C4 | C5 |
| Fipronil | 6.7% | 6.7% | 6.7% | 6.7% | — | — |
| Permethrin | 50% | — | 50% | — | 50% | — |
| Pyriproxyfen | 2% | — | — | 3% | — | 3% |
| DGME qs | 100% w/v | 100% w/v | 100% w/v | 100% w/v | 100% w/v | 100% w/v |

Preparation Method

Place the solvent (diethylene glycol monoethyl ether or DGME) in a container; then add the permethrin (fluidized beforehand in a heated chamber), mix until complete solubilization is obtained. Introduce the pyriproxyfen, mix until complete solubilization of the pyriproxyfen (fluidized beforehand in a heated chamber) is obtained. Introduce the fipronil, mix until complete solubilization of the fipronil is obtained. Check the appearance: the solution obtained should be clear without particles.

I. Tests for Crystallization of a Composition According to the Invention

The objective of this study is to demonstrate the influence of a constituent in the crystallization phenomenon at ambient temperature on the glass plate model.

I.1. Test Conditions

Number of glass slides per composition: 5

Protocol:

place the glass slides on a dark-coloured support;
deposit approximately 300 μl of the test composition on each glass slide, while spreading it on the central part of the glass slide (so as to avoid overspill);
leave the glass slide for 24 h in an environment at ambient temperature (approximately 20° C.).

The following observations will be carried out:
the visual appearance (to the naked eye) of the compositions is observed after deposition thereof on a glass slide and reported in the observation table;
the visual appearance (to the naked eye) of the compositions is observed after 24 h at ambient temperature and is reported in the observation table while pointing out the possible presence and, where appropriate, the number of crystals present on the whole of the plate;
next, the plates are observed under polarized light and any crystals present are counted on the whole of the plate; an estimation of the size of the crystals is also carried out;
finally, the presence and the count of the crystals possibly present on each of the plates is reported in the observation table.

The counting instructions are the following:
when their number is between 0 and 20, the crystals are counted; above 20 crystals ">20" should be reported;
the homogeneity, in terms of crystal numbers, between the glass slides of the same sample is evaluated by visual comparison of the 5 glass slides of each sample.

I.2. Results

Observation at $t_0$: for all the compositions, the observation with the naked eye reveals no crystallization zone.

24 h after the deposition of the formulae on the plates, crystalline zones visible to the naked are observed on the plates of compositions C1, C2 and C3.

The microscopic observation of the plates on which these compositions C1, C2 and C3 were deposited reveals large crystalline zones located more on the edges of the deposits, with more than 20 crystals having sizes greater than 100 μm for compositions C2 and C3; composition C1 contains smaller crystals, the size of which can range up to 20 μm, and which are on the whole of the deposit.

For compositions R1, C4 and C5, the observation with the naked eye reveals no crystallization zone.

The microscopic observation of the deposits of these compositions reveals crystals of small size, ranging up to 4 μm for R1 and C5 and up to 6 μm for C4; the crystals are mainly located on the edges of the deposit.

These observations make it possible to classify the compositions according to their tendency to crystallize on a plate; thus, the classification of the composition which crystallizes the most to that which crystallizes the least is the following:

C2~C3>C1>C4>R1>C4>C5

I.3. Conclusion

These tests, and in particular the comparison of the behaviours of compositions R1 and C2, show that pyriproxyfen substantially reduces the crystallization of fipronil when it is in the presence of permethrin at high concentration.

II. Tests for Stability of a Composition According to the Invention

II.1. Composition Tested

| Composition | % w/v |
|---|---|
| Fipronil | 6.1% |
| Permethrin | 54.5% |
| Pyriproxyfen | 1.8% |
| BHA | 0.02% |
| BHT | 0.01% |
| Diethylene glycol monoethyl ether | qs 100 ml |

Preparation:

Place the solvent (diethylene glycol monoethyl ether) in a container; then add the permethrin (fluidized beforehand in a heated chamber), mix until complete solubilization is obtained. Introduce the pyriproxyfen, mix until complete solubilization of the pyriproxyfen (fluidized beforehand in a heated chamber) is obtained. Introduce the fipronil, mix until complete solubilization of the fipronil is obtained. Check the appearance, the solution obtained should be clear without particles.

Successively introduce the butylated hydroxyanisole (BHA) and the butylated hydroxytoluene (BHT). Mix until solubilization is obtained. Check the appearance, the solution obtained should be clear without particles.

Protocol:

The composition is stored in 10 ml transparent glass bottles at various temperatures (5° C., 25° C. and 40° C.), in incubators in the dark.

II.2. Results

The composition is stable after storage for 3 months at 25° C. and 40° C. When it is stored in the cold (5° C.), no crystal formation is observed after 1 month.

The invention claimed is:

1. A liquid topical veterinary pharmaceutical composition consisting of:
   between 2% and 10% by weight/volume of 5-amino-1-[2,6-dichloro-4-(trifluoromethyl)phenyl]-4-(trifluoromethylsulphinyl)-1H-pyrazole-3-carbonitrile (fipronil);
   at least 50% by weight/volume of permethrin;
   between 1% and 10% by weight/volume of pyriproxyfen;
   at least one antioxidant chosen from ethyl or propyl gallate, α-tocopherol, ascorbic acid, ascorbyl palmitate, monothioglycerol, butylated hydroxytoluene (BHT) and butylated hydroxyanisole (BHA);
   in solution in an organic solvent chosen from propylene glycol monomethyl ether, dipropylene glycol n-butyl ether, ethylene glycol monomethyl ether, ethylene glycol monoethyl ether, diethylene glycol monoethyl ether, propylene glycol, and mixtures thereof.

2. The liquid topical veterinary pharmaceutical composition according to claim 1, characterized in that it consists of:
   between 5% and 10% by weight/volume of fipronil;
   between 50% and 70% by weight/volume of permethrin;
   between 1% and 10% by weight/volume of pyriproxyfen;
   between 0.005% and 2% by weight/volume of BHT and/or BHA;
   in solution in an organic solvent chosen from propylene glycol monomethyl ether, dipropylene glycol n-butyl ether, ethylene glycol monomethyl ether, ethylene glycol monoethyl ether, diethylene glycol monoethyl ether, propylene glycol, and mixtures thereof.

3. The liquid topical veterinary pharmaceutical composition according to claim 1, characterized in that it consists of:
   between 5% and 10% by weight/volume of fipronil;
   between 50% and 60% by weight/volume of permethrin;
   between 1% and 5% by weight/volume of pyriproxyfen;
   between 0.005% and 2% by weight/volume of BHT and/or BHA;
   in solution in an organic solvent chosen from propylene glycol monomethyl ether, dipropylene glycol n-butyl ether, ethylene glycol monomethyl ether, ethylene glycol monoethyl ether, diethylene glycol monoethyl ether, propylene glycol, and mixtures thereof.

4. The liquid topical veterinary pharmaceutical composition according to claim 1, characterized in that said organic solvent is diethylene glycol monoethyl ether.

5. The liquid topical veterinary pharmaceutical composition according to claim 1, characterized in that it consists of:

| | |
|---|---|
| Fipronil | 6.7% |
| Permethrin | 50% |
| Pyriproxyfen | 2% |
| BHA | 0.03% |
| BHT | 0.02% |
| Diethylene glycol monoethyl ether | qs 100 ml | composition expressed as percentage by weight relative to the total volume of the composition.

6. The liquid topical veterinary pharmaceutical composition according to claim 1, characterized in that it is packaged in a single-dose pipette.

7. A method for protection against and/or treatment of infestation by external parasites in domestic animals comprising the topical administration of the liquid topical veterinary pharmaceutical composition according to claim 1.

8. The method according to claim 7 wherein said liquid topical veterinary pharmaceutical composition is administered by spot-on application.

* * * * *